(12) United States Patent
Taniguchi et al.

(10) Patent No.: US 12,383,884 B2
(45) Date of Patent: Aug. 12, 2025

(54) POLYAMIDE MEDIUM FOR PURIFYING PROTEIN-CONTAINING SOLUTION AND METHOD FOR PRODUCING POLYAMIDE MEDIUM

(71) Applicant: ASAHI KASEI MEDICAL CO., LTD., Tokyo (JP)

(72) Inventors: Hiroki Taniguchi, Tokyo (JP); Junji Hidaka, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 838 days.

(21) Appl. No.: 17/601,834

(22) PCT Filed: Apr. 7, 2020

(86) PCT No.: PCT/JP2020/015741
§ 371 (c)(1),
(2) Date: Oct. 6, 2021

(87) PCT Pub. No.: WO2020/209267
PCT Pub. Date: Oct. 15, 2020

(65) Prior Publication Data
US 2022/0212167 A1   Jul. 7, 2022

(30) Foreign Application Priority Data

Apr. 8, 2019   (JP) .................................. 2019-073514
Nov. 6, 2019   (JP) .................................. 2019-201725

(51) Int. Cl.
*B01J 20/26*   (2006.01)
*B01J 20/28*   (2006.01)
(Continued)

(52) U.S. Cl.
CPC ....... *B01J 20/262* (2013.01); *B01J 20/28033* (2013.01); *B01J 20/28054* (2013.01);
(Continued)

(58) Field of Classification Search
CPC ................ B01J 20/262; B01J 20/28033; B01J 20/28054; B01J 20/28038; B01J 20/28042;
(Continued)

(56) References Cited

U.S. PATENT DOCUMENTS

| 4,512,896 A | 4/1985 | Gershoni |
| 4,693,985 A | 9/1987 | Degan et al. |

(Continued)

FOREIGN PATENT DOCUMENTS

| CN | 1355064 A | 6/2002 |
| CN | 104801204 A | 7/2015 |

(Continued)

OTHER PUBLICATIONS

Kusano et al. JP2012187448A English Translation (Year: 2018).*
(Continued)

*Primary Examiner* — Waqaas Ali
(74) *Attorney, Agent, or Firm* — GREENBLUM & BERNSTEIN, P.L.C.

(57) ABSTRACT

A method for producing a polyamide medium for purifying a protein-containing solution, comprising: a step of treating a polyamide medium before a treatment with an acidic or alkaline aqueous solution, with an acidic or alkaline aqueous solution.

6 Claims, 1 Drawing Sheet

(51) Int. Cl.
*C07K 1/34* (2006.01)
*C07K 16/40* (2006.01)

(52) U.S. Cl.
CPC ............... *C07K 1/34* (2013.01); *C07K 16/40* (2013.01); *C07K 2317/21* (2013.01)

(58) Field of Classification Search
CPC ...... C07K 1/34; C07K 16/40; C07K 2317/21; C07K 16/00; B01D 2311/18; B01D 2321/164; B01D 15/20; B01D 15/34; B01D 65/02; B01D 71/56; C08J 2377/00; C08J 7/12; C08G 69/46
See application file for complete search history.

(56) References Cited

U.S. PATENT DOCUMENTS

| | | |
|---|---|---|
| 5,644,036 A | 7/1997 | Ramage et al. |
| 2005/0205489 A1 | 9/2005 | Siwak et al. |
| 2010/0197817 A1 | 8/2010 | Bui et al. |
| 2012/0029176 A1 | 2/2012 | Yavorsky et al. |
| 2013/0056415 A1 | 2/2013 | Kozlov et al. |
| 2014/0116941 A1 | 5/2014 | Thorm et al. |
| 2018/0072769 A1 | 3/2018 | Olson et al. |
| 2018/0215786 A1 | 8/2018 | Kozlov et al. |
| 2019/0023736 A1 | 1/2019 | Yokohama et al. |

FOREIGN PATENT DOCUMENTS

| | | | | |
|---|---|---|---|---|
| CN | 107823915 A | 10/2017 | | |
| EP | 0 173 500 A1 | 3/1986 | | |
| JP | S61-124868 A | 6/1986 | | |
| JP | H05-271300 | 10/1993 | | |
| JP | H6-116810 | 4/1994 | | |
| JP | 2638680 B | 4/1997 | | |
| JP | H11-354093 | 12/1999 | | |
| JP | 2005-145852 | 6/2005 | | |
| JP | 2006-257397 A | 9/2006 | | |
| JP | 2008-108526 | 5/2008 | | |
| JP | 2009-173675 | 8/2009 | | |
| JP | 2009-242446 | 10/2009 | | |
| JP | 2012-187448 | 10/2012 | | |
| JP | 2012187448 A | * 10/2012 | | |
| JP | 2013-523394 | 6/2013 | | |
| JP | 2013-189427 | 9/2013 | | |
| JP | 2013-535683 | 9/2013 | | |
| JP | 2018-00772 | 3/2018 | | |
| JP | 2018-510166 | 4/2018 | | |
| JP | 6455851 B | 12/2018 | | |
| WO | 84/003055 A | 8/1984 | | |
| WO | 84/004696 | 12/1984 | | |
| WO | WO-2016013609 A1 * | 1/2016 | ............ | B01D 15/362 |
| WO | WO-2017017994 A1 * | 2/2017 | ............ | B01D 61/025 |

OTHER PUBLICATIONS

Search Report issued in EP Patent Application No. 20788609.4, Jun. 2, 2022.
"HLC Mailgram", Tosoh Corporation, Aug. 25, 2003, vol. 97, No. 3, p. 10, English translation.
ISR issued in WIPO Patent Application No. PCT/JP2020/015741, Jun. 30, 2020, English translation.
IPRP issued in WIPO Patent Application No. PCT/JP2020/015741, Sep. 28, 2021, English translation.

* cited by examiner

POLYAMIDE MEDIUM FOR PURIFYING PROTEIN-CONTAINING SOLUTION AND METHOD FOR PRODUCING POLYAMIDE MEDIUM

TECHNICAL FIELD

The present invention relates to a method for producing a polyamide medium for purifying a protein-containing solution, a method for purifying a protein-containing solution, and a polyamide medium for purifying a protein-containing solution.

BACKGROUND ART

In recent years, biopharmaceuticals to which a protein is applied have attracted attention in medicaments.

Among them, immunoglobulins, that is, antibodies, have been attracting particular attention, and the utility value thereof is increasing in applications such as medicaments, diagnostic drugs, or separation and purification materials for corresponding antigen proteins.

The antibody is a physiologically active substance that controls an immune reaction, and is obtained from the blood of an immunized animal, a cell culture solution of a cell possessing an antibody-producing ability, or an ascitic culture solution of an animal.

Such an antibody-containing blood, cell culture solution, and ascitic culture solution include a protein other than the antibody, or a complicated contaminant component derived from a stock solution used in cell culture (hereinafter, these may be referred to as contaminants), and the contaminants are removed through a multi-stage step.

As a method for removing a contaminant from the blood, cell culture solution, and ascitic culture solution, conventionally, a method using an ion exchange column or a hydrophobic gel utilizing an adsorption mechanism (see, for example, Non Patent Literature 1 below), and further, a method using a polyamide-containing shaped body (see, for example, Patent Literature 1 below) have been proposed, for example.

As another form of the method for removing a contaminant, a method for removing a contaminant using a size exclusion mechanism has proposed, including a method using a size exclusion column (see, for example, Patent Literature 2 below), or a method involving filtering using a nanofilter.

CITATION LIST

Patent Literature

[Patent Literature 1] Japanese Patent No. 6455851
[Patent Literature 2] Japanese Patent No. 2638680

Non Patent Literature

[Non Patent Literature 1] HLC MAILGRAM, Tosoh Corporation, Aug. 25, 2003, Vol. 97, No. 3, p. 10

SUMMARY OF INVENTION

Technical Problem

However, both the method for removing a contaminant utilizing an adsorption mechanism and the method for removing a contaminant using a size exclusion mechanism described above have the following problem: adsorption of a target protein also occurs, which reduces the recovery rate of the target protein.

Therefore, an object of the present invention is to provide a method for producing a polyamide medium for purifying a protein-containing solution having a higher recovery rate of a target protein, and a polyamide medium for purifying a protein-containing solution.

Another object is to provide a method for producing a polyamide medium for purifying a protein-containing solution and a polyamide medium for purifying a protein-containing solution, wherein the strength of the polyamide medium is maintained even after a treatment with an acid or an alkali.

Yet another object is to provide a method for purifying a protein-containing solution using the polyamide medium.

Solution to Problem

As a result of diligent research to solve the problems described above, the present inventors have found that by carrying out a predetermined treatment of a polyamide medium, a polyamide medium for purifying a protein-containing solution that can solve the problems of the prior art described above can be obtained, and have completed the present invention.

Specifically, the present invention is as follows.

[1]
A method for producing a polyamide medium for purifying a protein-containing solution, comprising: a step of treating a polyamide medium before a treatment with an acidic or alkaline aqueous solution, with an acidic or alkaline aqueous solution.

[2]
The method for producing a polyamide medium for purifying a protein-containing solution according to [1] above, wherein the polyamide medium is a porous body.

[3]
The method for producing a polyamide medium for purifying a protein-containing solution according to [2] above, wherein the porous body is a porous body in the form of a membrane.

[4]
The method for producing a polyamide medium for purifying a protein-containing solution according to any one of [1] to [3] above, wherein the acidic or alkaline aqueous solution is an acidic aqueous solution having a pH of 5 or less.

[5]
The method for producing a polyamide medium for purifying a protein-containing solution according to any one of [1] to [3] above, wherein the acidic or alkaline aqueous solution is an alkaline aqueous solution having a pH of 10 or more.

[6]
The method for producing a polyamide medium for purifying a protein-containing solution according to any one of [1] to [5] above, wherein the protein-containing solution is an antibody-containing solution.

[7]
A method for purifying a protein-containing solution, comprising:
 a step of contacting a protein-containing solution with a polyamide medium for purifying a protein-containing solution treated with an acidic or alkaline aqueous solution.

[7-1]
A method for purifying a protein-containing solution, comprising:
a step of contacting a protein-containing solution with a polyamide medium for purifying a protein-containing solution treated with an acidic or alkaline aqueous solution obtained by the method for producing a polyamide medium for purifying a protein-containing solution according to any one of [1] to [6] above.

[8]
The method for purifying a protein-containing solution according to [7] or [7-1] above, wherein the step of contacting a protein-containing solution with a polyamide medium is
a step of filtering the protein-containing solution with the polyamide medium.

[9]
A method for purifying a protein-containing solution, comprising:
a step of treating a polyamide medium before an alkali treatment, with an alkaline aqueous solution having a pH of 10 or more under conditions of 4° C. or more and 100° C. or less and 5 minutes or more and 70 hours or less; a step of washing the polyamide medium; and a step of contacting a protein-containing solution with the polyamide medium after the cleaning.

[9-1]
A method for purifying a protein-containing solution, comprising:
a step of treating a polyamide medium before an alkali treatment, with an alkaline aqueous solution having a pH of 13 or more under conditions of 10° C. or more and 30° C. or less and 0.5 hours or more and 40 hours or less;
a step of cleaning the polyamide medium; and
a step of contacting a protein-containing solution with the polyamide medium.

[10]
A polyamide medium for purifying a protein-containing solution, wherein
a sum of an amino group and a carboxyl group on a surface of the polyamide medium is 1.01 times or more larger than a sum of an amino group and a carboxyl group inside the polyamide medium.

[10-1]
A polyamide medium for purifying a protein-containing solution obtained by the method for producing a polyamide medium for purifying a protein-containing solution according to any one of [1] to [6] above,
wherein
a sum of an amino group and a carboxyl group on a surface of the polyamide medium is 1.01 times or more larger than a sum of an amino group and a carboxyl group inside the polyamide medium.

[11]
A polyamide medium for purifying a protein-containing solution, wherein
a number average molecular weight of a polymer on a surface of the polyamide medium, Mn(S), and
a number average molecular weight of a polymer inside the polyamide medium, Mn(I), are
represented by the following formula:

$Mn(S)/Mn(I) \leq 0.99$.

[11-1]
A polyamide medium for purifying a protein-containing solution obtained by the method for producing a polyamide medium for purifying a protein-containing solution according to any one of [1] to [6] above,
wherein
a number average molecular weight of a polymer on a surface of the polyamide medium, Mn(S), and
a number average molecular weight of a polymer inside the polyamide medium, Mn(I), are represented by the following formula:

$Mn(S)/Mn(I) \leq 0.99$.

[12]
A method for purifying a protein-containing solution, comprising:
a step of contacting a protein-containing solution with the polyamide medium for purifying a protein-containing solution according to [10], [10-1], [11] or [11-1] above.

[13]
The method for purifying a protein-containing solution according to [12] above, wherein
the step of contacting a protein-containing solution with the polyamide medium for purifying a protein-containing solution is a step of filtering the protein-containing solution with the polyamide medium.

[14]
A method for producing a polyamide medium for removing an antibody aggregate, comprising:
a step of immersing a polyamide medium before immersion in an alkaline aqueous solution, in an acidic aqueous solution having a pH of 5 or less or an alkaline aqueous solution having a pH of 10 or more for 5 minutes or more.

[15]
The method for producing a polyamide medium for removing an antibody aggregate according to [14] above, wherein the polyamide medium is a porous body.

[16]
The method for producing a polyamide medium for removing an antibody aggregate according to [15] above, wherein the porous body is a porous body in the form of a membrane.

[17]
The method for producing a polyamide medium for removing an antibody aggregate according to any one of [14] to [16] above, wherein the alkaline aqueous solution is a sodium hydroxide aqueous solution or a potassium hydroxide aqueous solution.

[18]
The method for producing a polyamide medium for removing an antibody aggregate according to any one of [14] to [17] above, wherein the antibody aggregate is a monoclonal antibody aggregate.

[19]
A method for recovering an antibody solution having an improved antibody monomer purity, comprising:
a step of contacting an antibody solution including an antibody aggregate with a polyamide medium treated with an acidic or alkaline aqueous solution.

[19-1]
A method for recovering an antibody solution having an improved antibody monomer purity, comprising a step of contacting an antibody solution including an antibody aggregate with a polyamide medium obtained by the method for producing a polyamide medium for removing an antibody aggregate according to any one of [14] to [18] above.

[20]
A method for removing an antibody aggregate from an antibody solution, comprising:

a step of contacting an antibody solution including an antibody aggregate with a polyamide medium treated with an acidic or alkaline aqueous solution.

[20-1]

A method for removing an antibody aggregate from an antibody solution, comprising:
a step of contacting an antibody solution including an antibody aggregate with a polyamide medium obtained by the method for producing a polyamide medium for removing an antibody aggregate according to any one of [14] to [18] above.

[21]

The method for recovering an antibody solution having an improved antibody monomer purity according to [19] or [19-1] above, wherein the antibody is a monoclonal antibody.

[22]

The method for removing an antibody aggregate from an antibody solution according to [20] or [20-1] above, wherein the antibody is a monoclonal antibody.

[23]

A polyamide medium for removing an antibody aggregate, wherein
a sum of an amino group and a carboxyl group on a surface of the polyamide medium is 1.01 times or more larger than a sum of an amino group and a carboxyl group inside the polyamide medium.

[23-1]

A polyamide medium for removing an antibody aggregate obtained by the method for producing a polyamide medium for removing an antibody aggregate according to any one of [14] to [18] above, wherein a sum of an amino group and a carboxyl group on a surface of the polyamide medium is 1.01 times or more larger than a sum of an amino group and a carboxyl group inside the polyamide medium.

[24]

A polyamide medium for purifying removing an antibody aggregate, wherein
a number average molecular weight of a polymer on a surface of the polyamide medium, $Mn(S)$, and
a number average molecular weight of a polymer inside the polyamide medium, $Mn(I)$, are
represented by the following formula:

$$Mn(S)/Mn(I) \leq 0.99.$$

[24-1]

A polyamide medium for purifying removing an antibody aggregate obtained by the method for producing a polyamide medium for removing an antibody aggregate according to any one of [14] to [18] above, wherein a number average molecular weight of a polymer on a surface of the polyamide medium, $Mn(S)$, and a number average molecular weight of a polymer inside the polyamide medium, $Mn(I)$, are
represented by the following formula:

$$Mn(S)/Mn(I) \leq 0.99.$$

[25]

A method for recovering an antibody solution having an improved purity, comprising:
a step of contacting the polyamide medium for removing an antibody aggregate according to [23], [23-1], [24] or [24-1] above with an antibody solution including an antibody aggregate.

[26]

A method for removing an antibody aggregate from an antibody solution, comprising:
a step of contacting the polyamide medium for removing an antibody aggregate according to [23], [23-1], [24] or [24-1] above with an antibody solution including an antibody aggregate.

Advantageous Effects of Invention

According to one aspect of the present invention, a method for producing a polyamide medium for purifying a protein-containing solution having a high recovery rate of a target protein can be provided. In addition, in one embodiment, a method for purifying a protein-containing solution using a polyamide medium obtained by the above production method can be provided. Further, in another aspect, a polyamide medium for purifying a protein-containing solution can be provided.

DESCRIPTION OF EMBODIMENTS

Figure 1:
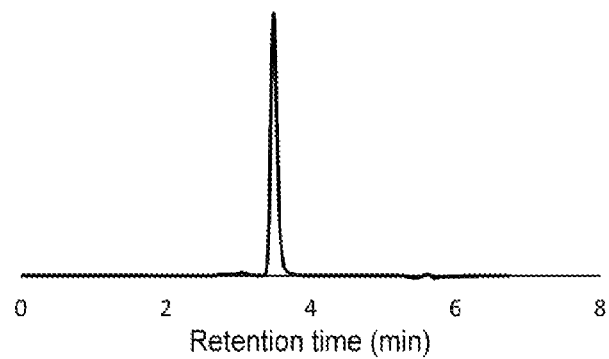
FIG. 1 shows a chromatography chart of an antibody-containing solution including an antibody monomer and an antibody aggregate according to Example 1.

Hereinafter, an embodiment of the present invention (hereinafter, also referred to as "the present embodiment") will be described in detail.

It should be noted that the following embodiment is illustrative of the present invention for description, and the present invention is not intended to be limited to the following contents. The present invention can be practiced with various modifications within the scope of the gist thereof.

[Method for Producing Polyamide Medium for Purifying Protein-Containing Solution]

The method for producing a polyamide medium for purifying a protein-containing solution according to the present embodiment includes a step of treating a polyamide raw material with an acidic or alkaline aqueous solution.

By having the configuration described above, a polyamide medium having a high recovery rate of a target protein can be obtained.

Here, the polyamide raw material, that is, the polyamide medium before a treatment with an acidic or alkaline aqueous solution refers to an untreated polyamide medium before carrying out the step of treating a polyamide raw material with an acidic or alkaline aqueous solution. The polyamide raw material may be a medium including only a polyamide or a medium including a compound other than a polyamide.

By purifying a protein-containing solution using a polyamide medium for purifying a protein-containing solution obtained by the production method of the present embodiment, the amount of the target protein adsorbed on the polyamide medium can be reduced, and the target protein can be recovered with a high recovery rate.

As one mechanism for creating the effect that the target protein can be recovered with a high recovery rate, it is considered that an amide bond on the polyamide surface is hydrolyzed by treating the polyamide medium before a treatment with an acidic or alkaline aqueous solution and a carboxy group or an amino group, which is a hydrophilic functional group, appears, thereby reducing protein adsorption on the polyamide medium, but the present invention is not bound by this mechanism.

It is a preferable embodiment that the polyamide medium for purifying a protein-containing solution obtained by the production method of the present embodiment maintains the strength in the state before a treatment with an acidic or alkaline aqueous solution.

That is, it is a preferable embodiment that the polyamide medium for purifying a protein-containing solution obtained by the production method of the present embodiment is a polyamide medium such that the amount of the target protein to be adsorbed on the polyamide medium is reduced, and such that the strength thereof is maintained as compared with that in the state before a treatment with an acidic or alkaline aqueous solution.

(Method for Producing Polyamide Medium for Removing Antibody Aggregate)

The polyamide medium for purifying a protein-containing solution obtained by the production method of the present embodiment may be a polyamide medium for removing an antibody aggregate.

That is, the polyamide medium for purifying a protein-containing solution according to the present embodiment may be a polyamide medium for purifying an antibody solution. Specifically, when an antibody-containing solution to be purified includes an antibody aggregate in addition to an antibody monomer, the aggregate may be removed by a polyamide medium.

When the method for producing a polyamide medium for purifying a protein-containing solution according to the present embodiment is a method for producing a polyamide medium for removing an antibody aggregate, the production method have a step of immersing a polyamide medium before being immersed in an alkaline aqueous solution, in an acidic aqueous solution having a pH of 5 or less or an alkaline aqueous solution having a pH of 10 or more for 5 minutes or more. In this way, a polyamide medium that can effectively remove an antibody aggregate can be obtained.

(Protein and Antibody)

In the present embodiment, the protein included in the protein-containing solution to be purified is not particularly limited as long as it is a protein that can recover the target protein with a high recovery rate by the polyamide medium obtained by the production method of the present embodiment. Examples thereof include, but are not limited to, albumin, globulin, and fibrinogen.

Preferable examples of the protein included in the protein-containing solution to be purified include an antibody. That is, preferable examples of the protein-containing solution to be purified include an antibody-containing solution.

By contacting a polyamide medium for purifying a protein-containing solution obtained by the production method of the present embodiment with a predetermined protein-containing solution including a protein aggregate, the protein aggregate is highly selectively removed, and a protein solution having an improved protein monomer purity can be recovered with a high recovery rate.

That is, by contacting an antibody solution including an antibody aggregate with the polyamide medium obtained by the production method of the present embodiment, the antibody aggregate is removed from the antibody solution, and the antibody solution having an improved antibody monomer purity can be recovered with a high recovery rate.

Examples of the antibody include a glycoprotein molecule (also referred to as a gamma globulin or an immunoglobulin) produced by a B lymphocyte as a mechanism for preventing infection in a vertebrate, as generally defined in biochemistry.

For example, the antibody in the antibody solution to be purified in the present embodiment can be used as a human medicament, and in such a case, has substantially the same structure as that of an antibody present in the body of a human to which the medicament is to be administered.

The antibody may be a human antibody or an antibody protein derived from a mammal such as a cow or a mouse other than a human.

The antibody may be a chimeric antibody protein with human IgG or a humanized antibody.

The chimeric antibody with human IgG refers to an antibody in which the variable regions are derived from a non-human organism such as a mouse, but the constant regions different therefrom are replaced with a human-derived immunoglobulin.

The humanized antibody refers to an antibody in which among the variable regions, the complementarity-determining regions (CDRs) are derived from a non-human organism, but the framework regions (FRs) different therefrom are derived from a human. A humanized antibody is even less immunogenic than a chimeric antibody.

In the present embodiment, the antibody class (isotype) and subclass are not particularly limited. For example, antibodies are classified into 5 classes, IgG, IgA, IgM, IgD, and IgE, depending on the difference in the structure of the constant region. However, when the polyamide medium for purifying a protein-containing solution obtained by the production method of the present embodiment is used as one for removing an antibody aggregate to remove an antibody aggregate to obtain an antibody solution having a high antibody monomer purity, the antibody included in the antibody solution to be purified may be of any of the 5 classes.

In a human antibody, IgG has four subclasses, IgG1 to IgG4, and IgA has two subclasses, IgA1 and IgA2. However, in the present embodiment, the antibody subclass may be any. An antibody-related protein such as an Fc fusion protein in which a protein binds to the Fc region can also be included in the antibody to be purified in the present embodiment.

Further, antibodies can also be classified by origin. However, the antibody to be purified in the present embodiment may be any of a natural human antibody, a recombinant human antibody produced by a genetic recombination technique, a monoclonal antibody, or a polyclonal antibody.

Among these antibodies, the monoclonal antibody is preferable as the antibody to be purified in the present embodiment in view of demand and importance as an antibody drug, but the present embodiment is not limited to this.

Examples of the antibody include a monoclonal antibody or a polyclonal antibody including any of IgM, IgD, IgG, IgA, and IgE. Further, the antibody may be derived from a plasma product or derived from a cell culture solution.

When an antibody is obtained by cell culture, an animal cell or a microorganism can be used as a cell.

The type of the animal cell is not particularly limited, and examples thereof include a CHO cell, an Sp2/0 cell, an NS0 cell, and a Vero cell, a PER.C6 cell.

The type of the microorganism is not particularly limited, and examples thereof include *Escherichia coli* and a yeast.

(Antibody Aggregate)

With regard to the case where the solution purified using a polyamide medium for purifying a protein-containing solution produced by the present embodiment is an antibody solution including an aggregate, examples of the antibody aggregate to be removed include a dimer in which two target antibody monomers are associated, a trimer in which three target antibody monomers are associated, a multimer in which four or more target antibody monomers are associated, or a mixture thereof.

Both a dimer and a trimer may be included in the multimer.

A protein other than the target antibody may be included in the antibody aggregate.

A protein aggregate may be an irreversible associated body or a reversible associated body.

(Polyamide Medium)

The polyamide constituting a polyamide medium before a treatment with an acidic or alkaline aqueous solution used in the method for producing a polyamide medium for purifying a protein-containing solution or the method for producing a polyamide medium for removing an antibody aggregate according to the present embodiment is a polymer constituted by repeating units including amide bonds. The monomer unit may be either an aliphatic polyamide or an aromatic polyamide, may be a mixture thereof, and may include a plurality of aliphatic monomers and aromatic monomers.

Examples of the polyamide include, but are not limited to, nylon 6, nylon 11, and nylon 12 obtained by a polycondensation reaction of ε-caprolactam, undecane caprolactam, and lauryl lactam, nylon 66 obtained by a copolycondensation reaction of hexamethylenediamine and adipic acid, nylon 610 obtained by a copolycondensation reaction of hexamethylenediamine and sebacic acid, nylon 6T obtained by a copolycondensation reaction of hexamethylenediamine and terephthalic acid, nylon 6I obtained by a copolycondensation reaction of hexamethylenediamine and isophthalic acid, nylon 9T obtained by a copolycondensation reaction of nonanediamine and terephthalic acid, nylon M5T obtained by the polycondensation reaction of methylpentadiamine and terephthalic acid, nylon 612 obtained by a copolycondensation reaction of ε-caprolactam and lauryl lactam, a polyamide obtained by a copolymerization reaction of paraphenylenediamine and terephthalic acid, and a polyamide obtained by a copolymerization reaction of metaphenylenediamine and isophthalic acid.

The polyamide medium before a treatment with an acidic or alkaline aqueous solution is not particularly limited, and examples thereof include a polyamide medium (excluding a polyamide medium having a graft chain). In another embodiment, examples thereof include a polyamide medium having no graft chain.

The weight average molecular weight of a polyamide constituting the polyamide medium before a treatment with an acidic or alkaline aqueous solution used in the method for producing a polyamide medium for purifying a protein-containing solution or the method for producing a polyamide medium for removing an antibody aggregate according to the present embodiment is not particularly limited, and a larger weight average molecular weight is more preferable in view of the strength of the polyamide medium. Specifically, the weight average molecular weight is preferably 2000 or more, more preferably 5000 or more, 10000 or more, 50000 or more, 60000 or more, 70000 or more, or 80000 or more, and further preferably 90000 or more, 95000 or more, or 100000 or more, in view of the strength of the polyamide medium.

The weight average molecular weight is preferably 2000000 or less, more preferably 1000000 or less, and further preferably 500000 or less, 300000 or less, or 200000 or less, in view of the spinnability and the amount of terminal functional groups when the polyamide medium is a fiber.

The weight average molecular weight of the polyamide can be measured by a known method such as GPC (Gel Permeation Chromatography).

The number average molecular weight of a polyamide constituting the polyamide medium before a treatment with an acidic or alkaline aqueous solution used in the method for producing a polyamide medium for purifying a protein-containing solution or the method for producing a polyamide medium for removing an antibody aggregate according to the present embodiment is not particularly limited, and a larger number average molecular weight is more preferable in view of the strength of the polyamide medium. Specifically, the number average molecular weight is preferably 1000 or more, more preferably 5000 or more, 6000 or more, 7000 or more, 8000 or more, 9000 or more, or 10000 or more, and further preferably 20000 or more, 25000 or more, or 30000 or more.

The number average molecular weight is preferably 1000000 or less, more preferably 500000 or less, and further preferably 100000 or less, 50000 or less, 40000 or less, or 30000 or less, in view of the spinnability and the amount of terminal functional groups when the polyamide medium is a fiber.

The number average molecular weight of the polyamide can be measured by a known method such as GPC (Gel Permeation Chromatography).

<Treatment Conditions for Method for Producing Polyamide Medium for Purifying Protein-Containing Solution>

The method for producing a polyamide medium for purifying a protein-containing solution according to the present embodiment includes a step of treating a polyamide medium before a predetermined treatment as a raw material with an acidic or alkaline aqueous solution.

In the method for producing a polyamide medium according to the present embodiment, a change that occurs in the polyamide as a raw material is not particularly limited, and examples thereof include hydrolysis and introduction of a functional group. Examples of the functional group to be introduced include a hydroxy group, a carboxy group, an amino group, a sulfo group, an aldehyde group, a carbonyl group, and a nitro group.

The treatment method may be immersion and, in the case of a porous body, may be liquid passage.

In the case of a treatment with an acidic aqueous solution, the pH of the acidic aqueous solution is, as the upper limit, preferably 5 or less, more preferably 4 or less, 3 or less, 2 or less, 1.5 or less, or the like in view of the progress rate of hydrolysis. As an example of the lower limit, the pH is 1.0 or more in view of the strength of the polyamide medium.

Examples of the acidic aqueous solution include aqueous solutions of an inorganic acid such as hydrochloric acid, sulfuric acid, or nitric acid, and an organic acid such as trifluoroacetic acid. The acidic aqueous solution may include a compound other than the inorganic acid or the organic acid.

The immersion time in the case of immersion in an acidic aqueous solution as a treatment method is, as the lower limit, preferably 5 minutes or more, more preferably 10 minutes or more, 20 minutes or more, 30 minutes or more, 40 minutes or more, 50 minutes or more, or 55 minutes or more in view of decomposition of the amide bond on the surface of the polyamide medium before a predetermined treatment as a raw material, and further preferably, sequentially 1 hour or more, 2 hours or more, 3 hours or more, 5 hours or more, 10 hours or more, 15 hours or more, 20 hours or more, 40 hours or more, or 70 hours or more can be appropriately selected depending on the type and the form of the polyamide medium and the type of the antibody to be applied.

As the upper limit, 70 hours or less, 40 hours or less, 20 hours or less, 15 hours or less, 10 hours or less, 5 hours or less, 3 hours or less, 2 hours or less, 1 hour or less, 30 minutes or less, 20 minutes or less, or 10 minutes or less can be appropriately selected in view of the strength of the polyamide medium.

The immersion temperature in the case of immersion in an acidic aqueous solution as a treatment method is, as the lower limit, preferably 4° C. or more, more preferably 10° C. or more or 15° C. or more, and further preferably 20° C. or more in view of the progress rate of decomposition of the amide bond on the surface of the polyamide medium before the treatment as a raw material.

As the upper limit, the immersion temperature is preferably 100° C. or less, 80° C. or less, or 50° C. or less, more preferably 40° C. or less, and further preferably 30° C. or less in view of the strength of the polyamide medium.

The liquid passage time in the case of passage of an acidic aqueous solution as a treatment method is, as the lower limit, preferably 5 minutes or more, more preferably 10 minutes or more, 20 minutes or more, 30 minutes or more, 40 minutes or more, 50 minutes or more, or 55 minutes or more in view of decomposition of the amide bond on the surface of the polyamide medium before a predetermined treatment as a raw material, and further preferably, sequentially 1 hour or more, 2 hours or more, 3 hours or more, 5 hours or more, 10 hours or more, 15 hours or more, 20 hours or more, 40 hours or more, 70 hours or more, or the like can be appropriately selected depending on the type and the form of the polyamide medium and the type of the antibody to be applied.

As the upper limit, 70 hours or less, 40 hours or less, 20 hours or less, 15 hours or less, 10 hours or less, 5 hours or less, 3 hours or less, 2 hours or less, 1 hour or less, 30 minutes or less, 20 minutes or less, 10 minutes or less, or the like can be appropriately selected depending on the type and the form of the polyamide medium and the type of the antibody to be applied.

The liquid passage temperature in the case of passage of an acidic aqueous solution as a treatment method is, as the lower limit, preferably 4° C. or more, more preferably 10° C. or more or 15° C. or more, and further preferably 20° C. or more in view of the progress rate of decomposition of the amide bond on the surface of the polyamide medium before a predetermined treatment as a raw material.

As the upper limit, the liquid passage temperature is preferably 100° C. or less, 80° C. or less, or 50° C. or less, more preferably 40° C. or less, and further preferably 30° C. or less in view of the strength of the polyamide medium.

When the polyamide medium is treated with an alkaline aqueous solution, the pH of the alkaline aqueous solution is, as the lower limit, preferably pH 10.0 or more, more preferably 11.0 or more, further preferably 12.0 or more, further more preferably 12.5 or more, further more preferably 13.0 or more, and particularly preferably 13.5 or more in view of the decomposition efficiency of the amide bond on the surface of the polyamide medium.

As the upper limit, the pH is preferably 14.0 or less, and more preferably 13.5 or less in view of the strength of the polyamide medium.

Examples of the alkaline aqueous solution include a sodium hydroxide aqueous solution, a potassium hydroxide aqueous solution, and a lithium hydroxide aqueous solution, and in view of acquisition cost, a sodium hydroxide aqueous solution or a potassium hydroxide aqueous solution is preferable.

The alkaline aqueous solution for treating the polyamide medium may include a compound other than sodium hydroxide, potassium hydroxide, and lithium hydroxide.

The immersion time in the case of immersion of the polyamide medium in an alkaline aqueous solution as a treatment method is, as the lower limit, preferably 5 minutes or more, more preferably 10 minutes or more, 20 minutes or more, or 30 minutes or more, and further preferably 40 minutes or more, 50 minutes or more, or 55 minutes or more in view of sufficiently causing hydrolysis of the amide bond on the surface of the polyamide medium before a predetermined treatment as a raw material, and sequentially 1 hour or more, 2 hours or more, 3 hours or more, 5 hours or more, 10 hours or more, 15 hours or more, 20 hours or more, 40 hours or more, 70 hours or more, or the like can be appropriately selected depending on the type and the form of the polyamide medium and the type of the protein to be applied.

As the upper limit, 70 hours or less, 40 hours or less, 20 hours or less, 15 hours or less, 10 hours or less, 5 hours or less, 3 hours or less, 2 hours or less, 1 hour or less, 30 minutes or less, 20 minutes or less, 10 minutes or less, or the like can be appropriately selected in view of the strength of the polyamide medium.

The immersion temperature in the case of immersion of the polyamide medium in an alkaline aqueous solution as a treatment method is, as the lower limit, preferably 4° C. or more, more preferably 10° C. or more or 15° C. or more, and further preferably 20° C. or more in view of the progress rate of decomposition of the amide bond on the surface of the polyamide medium before a predetermined treatment as a raw material. As examples of the upper limit, the immersion temperature is preferably 100° C. or less, 80° C. or less, or 50° C. or less, more preferably 40° C. or less, and further preferably 30° C. or less in view of the strength of the polyamide medium.

The liquid passage time in the case of passage of an alkaline aqueous solution through the polyamide medium as a treatment method is, as the lower limit, preferably 5 minutes or more, more preferably 10 minutes or more, 20 minutes or more, 30 minutes or more, 40 minutes or more, 50 minutes or more, or 55 minutes or more in view of decomposition of the amide bond on the surface of the polyamide medium before a predetermined treatment as a raw material, and further preferably, sequentially 1 hour or more, 2 hours or more, 3 hours or more, 5 hours or more, 10 hours or more, 15 hours or more, 20 hours or more, 40 hours or more, or 70 hours or more can be appropriately selected depending on the type and the form of the polyamide medium and the type of the antibody to be applied.

As the upper limit, 70 hours or less, 40 hours or less, 20 hours or less, 15 hours or less, 10 hours or less, 5 hours or less, 3 hours or less, 2 hours or less, 1 hour or less, 30 minutes or less, 20 minutes or less, 10 minutes or less, or the like can be appropriately selected in view of the strength of the polyamide medium.

The liquid passage temperature in the case of passage of an alkaline aqueous solution through the polyamide medium as a treatment method is, as the lower limit, preferably 4° C. or more, more preferably 10° C. or more or 15° C. or more, and further preferably 20° C. or more in view of the progress rate of decomposition of the amide bond on the surface of the polyamide medium before a predetermined treatment as a raw material. As the upper limit, the liquid passage temperature is preferably 100° C. or less, 80° C. or less, or 50° C. or less, more preferably 40° C. or less, and further preferably 30° C. or less in view of the strength of the polyamide medium.

The method for purifying a protein-containing solution according to the present embodiment preferably includes a step of treating a polyamide medium before an alkali treatment with an alkaline aqueous solution having a pH of 10 or more under conditions of 4° C. or more and 100° C. or less and 5 minutes or more and 70 hours or less, a step of washing the polyamide medium, and a step of contacting a protein-containing solution with the polyamide medium after the washing.

The method for purifying a protein-containing solution according to the present embodiment more preferably includes a step of treating a polyamide medium before an alkali treatment with an alkaline aqueous solution having a pH of 13 or more under conditions of 10° C. or more and 30° C. or less and 0.5 hours or more and 40 hours or less, and s step of washing the polyamide medium, and a step of contacting a protein-containing solution with the polyamide medium.

In this way, hydrolysis of the amide bond on the surface of the polyamide medium before a predetermined treatment as a raw material can be caused with a high efficiency and at a sufficient rate, and by purifying the protein-containing solution using the polyamide medium after the above treatment, the amount of the target protein adsorbed on the polyamide medium can be reduced to recover the target protein with a high recovery rate.

<Treatment Conditions for Method for Producing Polyamide Medium for Removing Antibody Aggregate>

When the method for producing a polyamide medium according to the present embodiment is particularly a method for producing a polyamide medium for removing an antibody aggregate, the polyamide medium before a predetermined treatment as a raw material is immersed in an acidic aqueous solution having a pH of 5 or less for 5 minutes or more or in an alkaline aqueous solution having a pH of 10 or more for 10 minutes or more.

In the method for producing a polyamide medium according to the present embodiment, a change that occurs in the polyamide as a raw material is not particularly limited, and examples thereof include hydrolysis and introduction of a functional group. Examples of the functional group to be introduced include a hydroxy group, a carboxy group, an amino group, a sulfo group, an aldehyde group, a carbonyl group, and a nitro group.

In the case of a treatment with an acidic aqueous solution, the pH of the acidic aqueous solution is, as the upper limit, preferably 5 or less, more preferably 4 or less, 3 or less, 2 or less, or 1.5 or less in view of the progress rate of decomposition of the amide bond on the surface of the polyamide medium. As the lower limit, the pH is preferably 1.0 or more in view of the strength of the polyamide medium.

Examples of the acidic aqueous solution include aqueous solutions of an inorganic acid such as hydrochloric acid, sulfuric acid, or nitric acid, and an organic acid such as trifluoroacetic acid. The acidic aqueous solution may include a compound other than the inorganic acid or the organic acid.

The immersion time in the case of immersion in an acidic aqueous solution as a treatment method is, as the lower limit, preferably 5 minutes or more, more preferably 10 minutes or more, 20 minutes or more, 30 minutes or more, 40 minutes or more, 50 minutes or more, or 55 minutes or more in view of decomposition of the amide bond on the surface of the polyamide medium before a predetermined treatment as a raw material, and further preferably, sequentially 1 hour or more, 2 hours or more, 3 hours or more, 5 hours or more, 10 hours or more, 15 hours or more, 20 hours or more, 40 hours or more, 70 hours or more, or the like can be appropriately selected depending on the type and the form of the polyamide medium and the type of the antibody to be applied.

As the upper limit, 70 hours or less, 40 hours or less, 20 hours or less, 15 hours or less, 10 hours or less, 5 hours or less, 3 hours or less, 2 hours or less, 1 hour or less, 30 minutes or less, 20 minutes or less, 10 minutes or less, or the like can be appropriately selected in view of the strength of the polyamide medium.

The immersion temperature in the case of immersion in an acidic aqueous solution as a treatment method is, as the lower limit, preferably 4° C. or more, more preferably 10° C. or more or 15° C. or more, and further preferably 20° C. or more in view of the progress rate of decomposition of the amide bond on the surface of the polyamide medium before a predetermined treatment as a raw material.

As the upper limit, the immersion temperature is preferably 100° C. or less, 80° C. or less, or 50° C. or less, more preferably 40° C. or less, and further preferably 30° C. or less in view of the strength of the polyamide medium.

The liquid passage time in the case of passage of an acidic aqueous solution as a treatment method is, as the lower limit, preferably 5 minutes or more, more preferably 10 minutes or more, 20 minutes or more, 30 minutes or more, 40 minutes or more, 50 minutes or more, or 55 minutes or more in view of decomposition of the amide bond on the surface of the polyamide medium before a predetermined treatment as a raw material, and further preferably, sequentially 1 hour or more, 2 hours or more, 3 hours or more, 5 hours or more, 10 hours or more, 15 hours or more, 20 hours or more, 40 hours or more, or 70 hours or more can be appropriately selected depending on the type and the form of the polyamide medium and the type of the antibody to be applied.

As the upper limit, 70 hours or less, 40 hours or less, 20 hours or less, 15 hours or less, 10 hours or less, 5 hours or less, 3 hours or less, 2 hours or less, 1 hour or less, 30 minutes or less, 20 minutes or less, or 10 minutes or less can be appropriately selected depending on the type and the form of the polyamide medium and the type of the antibody to be applied.

The liquid passage temperature in the case of passage of an acidic aqueous solution as a treatment method is, as the lower limit, preferably 4° C. or more, more preferably 10° C. or more or 15° C. or more, and further preferably 20° C. or more in view of the progress rate of decomposition of the amide bond on the surface of the polyamide medium before a predetermined treatment as a raw material.

As the upper limit, the liquid passage temperature is preferably 100° C. or less, 80° C. or less, or 50° C. or less, more preferably 40° C. or less, and further preferably 30° C. or less in view of the strength of the polyamide medium.

When the polyamide medium is treated with an alkaline aqueous solution, the pH of the alkaline aqueous solution is, as the lower limit, preferably pH 10.0 or more, more preferably 11.0 or more, further preferably 12.0 or more, further more preferably 12.5 or more, further more preferably 13.0 or more, and particularly preferably 13.5 or more in view of the decomposition efficiency of the amide bond on the surface of the polyamide medium.

As the upper limit, the pH is preferably 14 or less, and more preferably 13.5 or less in view of the strength of the polyamide medium.

Preferable examples of the alkaline aqueous solution include a sodium hydroxide aqueous solution, a potassium hydroxide aqueous solution, and a lithium hydroxide aqueous solution.

The alkaline aqueous solution may include a compound other than sodium hydroxide, potassium hydroxide, and lithium hydroxide.

The immersion time in the case of immersion of the polyamide medium in an alkaline aqueous solution as a treatment method is, as the lower limit, preferably 5 minutes or more, more preferably 10 minutes or more, further preferably 20 minutes or more, further more preferably 30 minutes or more, 40 minutes or more, 50 minutes or more, or 55 minutes or more in view of sufficiently causing hydrolysis of the amide bond on the surface of the polyamide medium as a raw material, and more further preferably, sequentially 1 hour or more, 2 hours or more, 3 hours or more, 5 hours or more, 10 hours or more, 15 hours or more, 20 hours or more, 40 hours or more, or the like can be appropriately selected depending on the type and the form of the polyamide medium and the type of the antibody to be applied.

As the upper limit, 40 hours or less, 20 hours or less, 15 hours or less, 10 hours or less, 5 hours or less, 3 hours or less, 2 hours or less, 1 hour or less, 30 minutes or less, 20 minutes or less, 10 minutes or less, or the like can be appropriately selected in view of the strength of the polyamide medium.

The immersion temperature in the case of immersion of the polyamide medium in an alkaline aqueous solution as a treatment method is, as the lower limit, preferably 4° C. or more, more preferably 10° C. or more, further preferably 15° C. or more, and further more preferably 20° C. or more in view of the progress rate of decomposition of the amide bond on the surface of the polyamide medium before a predetermined treatment as a raw material.

As the upper limit, the immersion temperature is preferably 100° C. or less, 80° C. or less, or 50° C. or less, more preferably 40° C. or less, and further preferably 30° C. or less in view of the strength of the polyamide medium.

The liquid passage time in the case of passage of an alkaline aqueous solution through the polyamide medium as a treatment method is, as the lower limit, preferably 5 minutes or more, more preferably 10 minutes or more, 20 minutes or more, 30 minutes or more, 40 minutes or more, 50 minutes or more, or 55 minutes or more in view of decomposition of the amide bond on the surface of the polyamide medium before a predetermined treatment as a raw material, and further preferably, sequentially 1 hour or more, 2 hours or more, 3 hours or more, 5 hours or more, 10 hours or more, 15 hours or more, 20 hours or more, 40 hours or more, 70 hours or more, or the like can be appropriately selected depending on the type and the form of the polyamide medium and the type of the antibody to be applied.

As the upper limit, 70 hours or less, 40 hours or less, 20 hours or less, 15 hours or less, 10 hours or less, 5 hours or less, 3 hours or less, 2 hours or less, 1 hour or less, 30 minutes or less, 20 minutes or less, 10 minutes or less, or the like can be appropriately selected in view of the strength of the polyamide medium.

The liquid passage temperature in the case of passage of an alkaline aqueous solution through the polyamide medium as a treatment method is, as the lower limit, preferably 4° C. or more, more preferably 10° C. or more, further preferably 15° C. or more, and further more preferably 20° C. or more in view of the progress rate of decomposition of the amide bond on the surface of the polyamide medium before a predetermined treatment as a raw material.

As the upper limit, the liquid passage temperature is preferably 100° C. or less, 80° C. or less, or 50° C. or less, more preferably 40° C. or less, and further preferably 30° C. or less in view of the strength of the polyamide medium.

The polyamide medium obtained by the production method of the present embodiment is preferably a porous body in view of the size of the surface area when a contaminant is removed by adsorption regardless of whether the polyamide medium is for purifying a protein-containing solution or for removing an antibody aggregate. Even when a contaminant is removed by size exclusion, the polyamide medium is preferably a porous body.

Examples of the form of the porous body include a membrane, a particle, a monolith, a capillary, and a sintered body, and specific examples thereof include a microporous hollow fiber membrane, a microporous flat membrane, a non-woven fabric, and a woven fabric. A porous body in the form of a membrane is preferable because the effect of purifying a protein-containing solution at a high speed by passage of the protein-containing solution can be obtained.

When the polyamide medium is a porous membrane, a smaller pore size of the porous membrane is more preferable in view of removing a contaminant by adsorption or size exclusion. The average pore size of the polyamide porous membrane is, as the upper limit, preferably 1000 nm or less, more preferably 500 nm or less, further preferably 400 nm or less, and further more preferably 300 nm or less. As the lower limit, the average pore size is preferably 1 nm or more, 5 nm or more, 10 nm or more, 20 nm or more, or 30 nm or more in view of the filtration rate.

[Method for Purifying Protein-Containing Solution]

The method for purifying a protein-containing solution according to the present embodiment includes a step of contacting a protein-containing solution with a polyamide medium treated with an acidic or alkaline aqueous solution.

Specifically, the method for purifying a protein-containing solution according to the present embodiment includes a step of contacting a protein-containing solution with a polyamide medium for purifying a protein-containing solution obtained by the method for producing a polyamide medium for purifying a protein-containing solution according to the present embodiment described above.

The step of contacting a protein-containing solution with a polyamide medium includes, for example, a step of passing a protein-containing solution through a polyamide medium and a step of immersing the polyamide medium in a protein solution, as will be described later. Examples of the step of passing a protein-containing solution through a polyamide medium include a step of filtering a protein-containing solution with a polyamide medium.

In this way, a protein-containing solution having an improved purity can be obtained.

Examples of the contaminant that can be removed by contacting a protein-containing solution with a polyamide medium include a protein aggregate, an antibody aggregate, host cell-derived proteins (HCP; Host Cell Proteins) in the biopharmaceutical production step, and a virus particle. The virus particle may have an envelope.

[Method for Recovering Antibody Solution and Method for Removing Antibody Aggregate from Antibody Solution]

The method for recovering an antibody solution and the method for removing an antibody aggregate from an antibody solution according to the present embodiment include a step of contacting an antibody solution including an antibody aggregate with a polyamide medium treated with an acidic or alkaline aqueous solution.

Specifically, the methods include a step of contacting a polyamide medium for removing an antibody aggregate obtained by the method for producing a polyamide medium for removing an antibody aggregate according to the present embodiment described above with an antibody solution including an antibody aggregate.

The step of contacting a polyamide medium with an antibody solution including an antibody aggregate includes, for example, a step of passing an antibody solution through a polyamide medium and a step of immersing a polyamide medium in an antibody solution, as will be described later. Examples of the step of passing a protein-containing solution through a polyamide medium include a step of filtering a protein-containing solution with a polyamide medium.

In this way, an antibody aggregate can be effectively removed from the antibody solution, and an antibody solution having an improved purity can be obtained.

In the present embodiment, the protein-containing solution may be an antibody solution, and the antibody solution may include an antibody aggregate. In that case, as described above, the antibody aggregate can be removed from the antibody solution to obtain an antibody solution having an improved antibody monomer purity with a high recovery rate.

When the protein-containing solution used in the present embodiment is an antibody solution, the antibody solution means a solution in which the target antibody is dissolved.

The solvent used for the antibody solution may be pure water or a buffer solution.

Examples of the type of a buffer solution that can be used as a solution include, but are not limited to, a buffer solution in which tris salt, an acetate, Tween, sorbitol, maltose, glycine, arginine, lysine, histidine, a sulfonate, a phosphate, citrate, or sodium chloride is dissolved.

The concentration of the antibody solution used in the present embodiment is not particularly limited as long as the antibody is dissolved in the solution.

The lower limit value of the concentration of the antibody solution is 0.01 mg/mL or more in one embodiment, 0.05 mg/mL or more in another embodiment, 0.1 mg/mL or more in yet another embodiment, 0.5 mg/mL or more in still another embodiment, 1.0 mg/mL or more in a further embodiment, and 5.0 mg/mL or more in a yet further embodiment.

The upper limit value of the concentration of the antibody solution is 100 mg/mL or less in one embodiment, 90 mg/mL or less in another embodiment, 80 mg/mL or less in yet another embodiment, 70 mg/mL or less in still another embodiment, 60 mg/mL or less in a further embodiment, 50 mg/mL or less in a yet further embodiment, 40 mg/mL or less in a still further embodiment, 30 mg/mL or less in another embodiment, 25 mg/mL or less in yet another embodiment, and 20 mg/mL or less in still another embodiment.

The concentration of the buffer solution is not particularly limited as long as the predetermined substance to be dissolved described above is dissolved therein.

The lower limit value of the concentration of the buffer solution is 0 mmol/L or more in one embodiment, 0.5 mmol/L or more in another embodiment, 1.0 mmol/L or more in yet another embodiment, 5 mmol/L or more in still another embodiment, 10 mmol/L or more in a further embodiment, 15 mmol/L or more in a yet further embodiment, and 25 mmol/L or more in a still further embodiment, depending on the type of the buffer solution.

The pH of the buffer solution is not particularly limited, and the lower limit value of the pH is 4.0 or more in one embodiment, 4.5 or more in another embodiment, 5.0 or more in yet another embodiment, 5.5 or more in still another embodiment, and 6.0 or more in a further embodiment, depending on the type of buffer solution. The upper limit value of the pH is 10.0 or less in one embodiment, 9.0 or less in another embodiment, 8.0 or less in yet another embodiment, 8.5 or less in still another embodiment, 8.0 or less in a further embodiment, 7.5 or less in a yet further embodiment, and 7.0 or less in a still further embodiment.

The electrical conductivity of the buffer solution is not particularly limited, and the lower limit value of the electrical conductivity is 0 mS/cm or more in one embodiment, 1 mS/cm or more in another embodiment, 2 mS/cm or more in yet another embodiment, 3 mS/cm or more in still another embodiment, 4 mS/cm or more in a further embodiment, and 5 mS/cm or more in a yet further embodiment depending on the type of buffer solution.

The upper limit value of the electrical conductivity is 100 mS/cm or less in one embodiment, 90 mS/cm or less in another embodiment, 80 mS/cm or less in yet another embodiment, 70 mS/cm or less in still another embodiment, 60 mS/cm or less in a further embodiment, 50 mS/cm or less in a yet further embodiment, and 40 mS/cm or less in a still further embodiment.

In the method for purifying a protein-containing solution according to the present embodiment, when an antibody aggregate is removed from an antibody solution as the protein-containing solution to recover an antibody solution having an improved antibody monomer purity, the polyamide medium and the antibody solution including the antibody aggregate are contacted with each other as described above.

The method for contacting the polyamide medium with the antibody solution is not particularly limited as long as the antibody solution can be contacted with the polyamide medium, and as described above, examples thereof include a method for passing the antibody solution through the polyamide medium and a method for immersing the polyamide medium in the antibody solution. Examples of the method for passing a protein-containing solution through a polyamide medium include a method for filtering a protein-containing solution with a polyamide medium.

Examples of the method for passing the antibody solution through the polyamide medium include a method for passing the antibody solution through the polyamide medium using a syringe, a pump, or the like. The method for passing the antibody solution through the polyamide medium may be any as long as the antibody solution caused to flow toward a predetermined portion of the polyamide medium passes through the polyamide medium and the antibody solution can be recovered from another portion of the polyamide medium. Before and after passing the antibody solution through the polyamide medium, a buffer solution may be passed through the polyamide medium separately from the antibody solution. Preferable examples of the method for passing a protein-containing solution through a polyamide medium include a method for filtering a protein-containing solution with a polyamide medium.

When the antibody solution is recovered, the whole antibody solution passed through the polyamide medium may be recovered, or a fraction may be obtained for each certain volume.

By collecting and combining fractions containing an antibody purified as described above, the antibody purified can be recovered.

The flow rate for passing the antibody solution through the polyamide medium is not particularly limited, and is, as the lower limit value, is 0.1 mL/min or more per mL of the polyamide medium in one embodiment, 0.5 mL/min or more in another embodiment, 1.0 mL/min or more in yet another embodiment, and 5 mL/min or more in still another embodiment, depending on the type of the antibody solution.

[Polyamide Medium for Purifying Protein-Containing Solution and Polyamide Medium for Removing Antibody Aggregate]

In the polyamide medium for purifying a protein-containing solution according to the present embodiment and the polyamide medium for removing an antibody aggregate according to the present embodiment, the sum (total number) of the amino groups and the carboxyl groups of the polymer on the surface of the polyamide medium is preferably 1.01 times or more larger than the sum (total number) of the amino groups and the carboxyl groups of the polymer inside the polymer medium.

In this way, a polyamide medium having high removal selectivity for a protein aggregate, for example, an antibody aggregate, and excellent strength characteristics can be obtained.

The polyamide medium described above can be obtained by the method for producing a polyamide medium for purifying a protein-containing solution according to the present embodiment and the method for producing a polyamide medium for removing an antibody aggregate according to the present embodiment described above, and as long as the condition of the sum of the amino groups and the carboxyl groups is satisfied, the polyamide production step can be arbitrarily selected, and is not limited to the production method of the present embodiment described above.

The surface also includes the surface of the pores when the polyamide medium is a porous body.

The polymer on the surface of the polyamide medium means a polymer present in the medium in the range from the surface to a depth of 10 nm, or 5 nm, 3 nm, or 2 nm, 1 nm, appropriately depending on the type and concentration of the acidic or alkaline aqueous solution used, the immersion time, the type of the antibody, the type of and form of the polyamide medium, and the like.

The polymer inside the polyamide medium means a polymer other than that on the surface of the polyamide medium defined above.

The polyamide medium for purifying a protein-containing solution and the polyamide medium for removing an antibody aggregate according to the present embodiment are polyamides and thus have functional groups of an amino group and a carboxy group at polymer ends.

The sum of the functional groups of amino groups and carboxyl groups on the surface of the polyamide medium and the sum of the functional groups inside the polyamide medium tend to be different, and in view of compatibility between the removal selectivity for a protein aggregate, for example, an antibody aggregate and the strength of the polyamide medium, the sum of the amino groups and the carboxyl groups on the surface is preferably 1.01 times or more, more preferably 1.02 times or more, further preferably 1.03 times or more, and further more preferably 1.04 times or more, 1.05 times or more, 1.06 times or more, 1.07 times or more, 1.08 times or more, 1.09 times or more, 1.1 times or more, 1.15 times or more, 1.2 times or more, 1.3 times or more, 1.4 times or more, 1.5 times or more, 2.0 times or more, 2.5 times or more, 3.0 times or more, 3.5 times or more, 4.0 times or more, 4.5 times or more, 5.0 times or more, 6.0 times or more, 7.0 times or more, 8.0 times or more, 9.0 times or more, 10.0 times or more, 15 times or more, 20 times or more, 30 times or more, 40 times or more, 50 times or more, or 100 times or more the sum of the amino groups and the carboxyl groups inside.

The sum of the functional groups of the amino group and the carboxyl group may be obtained by measuring the amounts of the amino groups and the carboxyl groups separately and calculating the total number thereof. In light of the mechanism in which an amino group and a carboxyl group are generated one-to-one by hydrolysis of an amide bond in the polyamide medium, the sum can be obtained by measuring the amount of either the amino group or the carboxyl group and doubling the amount.

In the polyamide medium for purifying a protein-containing solution and the polyamide medium for removing an antibody according to the present embodiment, the sum of the amino groups and the carboxyl groups on the surface can be controlled to be larger than the sum of the amino groups and carboxyl groups inside by any of the fold ratios shown above by appropriately setting the pH of the acidic or alkaline aqueous solution, adjustment of the immersion time in the alkaline aqueous solution, the immersion temperature, and the like.

The proportion of a predetermined functional group in the polyamide medium can be determined by the functional group density per mass.

The amount of functional groups in the whole polyamide medium can be quantified by, for example, NMR.

The amount of functional groups on the surface of the polyamide medium can be analyzed by a known method such as XPS (X-ray photoelectron spectroscopy).

In the polyamide medium for purifying a protein-containing solution and the polyamide medium for removing an antibody aggregate according to the present embodiment, the number average molecular weight of the polymer on the surface of the polyamide medium and the number average molecular weight of the polymer inside the polyamide medium may differ from each other, and the number average molecular weight of the polymer inside is preferably larger.

The surface also includes the surface of the pores when the polyamide medium is porous.

The polymer on the surface of the polyamide medium means a polymer present in the medium in the range from the surface to a depth of 10 nm, or 5 nm, 3 nm, or 2 nm, 1 nm, appropriately depending on the type and concentration of the acidic or alkaline aqueous solution used, the immersion time, the type of the antibody, the type of and form of the polyamide medium, and the like.

The polymer inside the polyamide medium means a polymer other than that on the surface of the polyamide medium.

The ratio of the number average molecular weights in that case can be represented by $Mn(S)/Mn(I)$, wherein $Mn(S)$ is the number average molecular weight of the polymer on the surface of the polyamide medium and $Mn(I)$ is the number average molecular weight of the polymer inside the polyamide medium, and the value of $Mn(S)/Mn(I)$ is preferably 0.99 or less in view of compatibility between the selectivity and the strength of a protein aggregate, for example, an antibody aggregate. That is, it is preferable that $Mn(S)/Mn(I)$ 0.99.

$Mn(S)/Mn(I)$ is more preferably 0.98 or less, further preferably 0.97 or less, further more preferably 0.96 or less, and further more preferably 0.95 or less, 0.94 or less, 0.93 or less, 0.92 or less, 0.91 or less, 0.90 or less, 0.88 or less, 0.86 or less, 0.84 or less, 0.82 or less, 0.80 or less, 0.75 or less, 0.70 or less, 0.60 or less, or 0.50 or less.

The number average molecular weight of the polyamide medium can be determined by a known method such as gel permeation chromatography, and in this case, it is the molecular weight in terms of the standard substance.

The polyamide medium of the present embodiment in which the ratio of the number average molecular weight of the polymer on the surface to the number average molecular weight of the polymer inside, (Mn(S)/Mn(I)), as described above is 0.99 or less can be obtained by the method for producing a polyamide medium for purifying a protein-containing solution and the method for producing a polyamide medium for removing an antibody aggregate according to the present embodiment described above. Specifically, a part of the bond chains of the surface polymer is broken by treating the polyamide medium with an acidic or alkaline aqueous solution, and thereby the number average molecular weight of the polymer inside tends to be larger.

The polyamide production step can be arbitrarily selected as long as the condition of the number average molecular weight ratio is satisfied, and the polyamide production step is not limited to the production method of the present embodiment described above. Specifically, in the polyamide medium for purifying a protein-containing solution and the polyamide medium for removing an antibody aggregate according to the present embodiment, the ratio of the number average molecular weight of the polymer on the surface to the number average molecular weight of the polymer inside can be controlled to be the numerical value shown above by appropriately setting the pH of the acidic or alkaline aqueous solution, adjustment of the immersion time in the alkaline aqueous solution, the immersion temperature, and the like.

EXAMPLES

Hereinafter, the present embodiment will be described in more detail with reference to specific Examples and Comparative Examples, but the present embodiment is not limited at all by the following Examples and Comparative Examples.

Example 1

(1) Immersion of Polyamide Membrane as Polyamide Medium in Alkaline Aqueous Solution A polyamide membrane as a porous polyamide medium having a circular shape having a diameter of 2.5 cm, a membrane thickness of 160 μm, and an average pore diameter of 0.2 μm (Whatman (registered trademark): 7402-002, manufactured by GE Healthcare, material: polyamide 66) was immersed in a 1.0 mol/L sodium hydroxide solution (pH 14) at room temperature for 24 hours.

Next, the polyamide membrane was washed with pure water 5 times to completely remove sodium hydroxide.

The two polyamide membranes obtained were set in a stainless holder KS-25 (manufactured by Advantech, effective membrane area of 3.8 cm$^2$) to obtain polyamide membrane 1.

The membrane thickness of the polyamide membrane was measured using a Digimatic Indicator ID-C112XBS (manufactured by Mitutoyo Corporation).

(2) Preparation of Antibody-Containing Solution as Protein-Containing Solution

A culture solution supernatant including 0.74 g/L of a monoclonal antibody expressed from CHO cell CRL12445 (hereinafter, sometimes abbreviated as CRL12445 antibody) was provided.

A culture solution including a monoclonal antibody-producing cell expressed from CRL12445 was filtered using a filtration membrane (manufactured by Asahi Kasei Medical Co., Ltd., trade name: BioOptimal (registered trademark) MF-SL) to obtain an antibody-containing solution (culture) including an impurity and an antibody (culture supernatant).

(3) Purification of Antibody-Containing Solution Using Affinity Column

The antibody-containing solution (culture supernatant) obtained in (2) above was added to a protein A column (column packed with MabSelect Sure manufactured by GE Healthcare Bio-Sciences Corp.) equilibrated with a phosphate buffer solution (20 mmol/L sodium phosphate+150 mmol/L NaCl (pH 8.0)) to adsorb the antibody on protein A.

Next, a phosphate buffer solution (20 mmol/L sodium phosphate+150 mmol/L NaCl (pH 8.0)) was passed through the column for washing, and then an elution buffer solution (100 mmol/L sodium citrate (pH 3.6)) was passed through the column to elute the antibody from the protein A column, and an antibody-containing solution in which an impurity was reduced to some extent was recovered.

When this antibody protein was measured by the method described in (8) below, only the peak of the antibody protein as a monomer (the peak of (3) in FIG. 2 described in (8) below) was confirmed, and the peaks of the aggregate (1) of trimers or higher multimers and the aggregate (2) of a dimer shown in FIG. 2 were not confirmed.

A pH meter, HM-30R (manufactured by DKK-TOA Corporation), was used to measure the pH of the buffer solution. The pH of the buffer solutions below was also measured in the same manner.

(4) Preparation of Antibody-Containing Solution Including Large Amount of Antibody Aggregate Hydrochloric acid was added to a part of the antibody-containing solution in which an impurity was reduced to some extent obtained in ((3) Purification of antibody using affinity column) above, the pH was adjusted to 2.5, and the resulting solution was maintained for 1 hour.

After that, the solution was neutralized using a sodium hydroxide aqueous solution to prepare an antibody-containing solution including a large amount of an antibody aggregate.

(5) Preparation of Antibody-Containing Solution Including Antibody Aggregate

A solution obtained by buffer-exchanging the antibody-containing solution in which an impurity was reduced to some extent obtained in ((3) Purification of antibody using affinity column) above to a 15 mmol/L tris-HCl buffer solution (pH 7.0, 5 mS/cm) including an arbitrary amount of sodium chloride and a solution obtained by buffer-exchanging the antibody-containing solution including a large amount of an aggregate obtained in ((4) Preparation of antibody-containing solution including large amount of antibody aggregate) above to a 15 mmol/L tris-HCl buffer solution (pH 7.0, 5 mS/cm) including an arbitrary amount of sodium chloride were mixed at an arbitrary ratio to prepare an antibody-containing solution including an antibody aggregate and an antibody monomer (hereinafter, sometimes abbreviated as "SM").

The electric conductivity of the buffer solutions was measured using an electric conductivity meter CM-40S (manufactured by DKK-TOA Corporation).

(6) Passage of Antibody-Containing Solution Through Polyamide Membrane

The antibody-containing solution (SM) including an antibody aggregate and an antibody monomer prepared in ((5) Preparation of antibody-containing solution including aggregate) above was passed through polyamide membrane 1 obtained by ((1) immersion of polyamide membrane in alkaline aqueous solution) above.

An AKTA purifier (manufactured by GE Healthcare), which is a separation/purification apparatus, was used to pass the antibody-containing solution, and the antibody-containing solution was passed to recover the antibody-containing solution.

The amount added was 13 mL (concentration of 4.8 mg/mL, total amount of antibody of 62.7 mg), and the flow rate was 3.9 mL/min.

(7) Evaluation of Aggregate Removal Performance

The aggregate removal performance was evaluated by the amount of the antibody aggregate removed and the amount of the antibody monomer recovered.

(8) Specific Evaluation Method for Aggregate Removal Performance

The antibody-containing solution recovered in ((6) Passage of antibody-containing solution through polyamide membrane) above and the antibody-containing solution (SM) including an antibody aggregate and an antibody monomer prepared in ((5) Preparation of antibody-containing solution including aggregate) above were measured using a size exclusion chromatography (SEC) apparatus under the following conditions.

The measurement results are shown in [Table 1] below, and a chromatographic chart of the antibody-containing solution including an antibody aggregate and an antibody monomer is shown in FIG. 1. FIG. 2 is an enlarged view of the chromatographic chart of FIG. 1.

Column: ACQUITY UPLC BEH200 SEC 1.7 μm (manufactured by Waters Corporation), Column temperature: 30° C., System: ACQUITY UPLC H CLASS (manufactured by Waters Corporation)

Mobile phase: 0.1 mol/L disodium hydrogen phosphate+ 0.2 mol/L L(+)-arginine aqueous solution (adjusted to pH 6.7 with hydrochloric acid)

Figure 2:
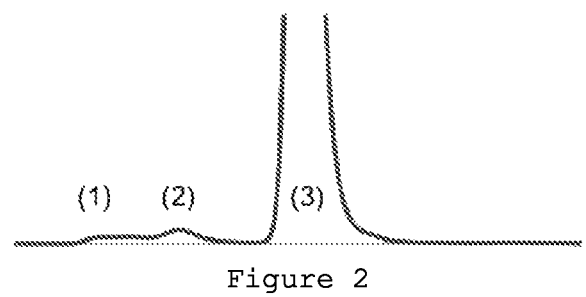
FIG. 2 shows an enlarged view of a peak portion of the chromatography chart of FIG. 1.

As shown in FIGS. 1 and 2, the antibody monomer (peak (3)), dimer (peak (2)), and trimer or higher multimer (peak (1)) aggregates separated.

(9) Calculation of Antibody Monomer Recovery Rate

The recovery rate of the antibody monomer was calculated from the results of antibody concentration and size exclusion chromatography using a spectrophotometer; SpectraMax Plus384 (manufactured by Molecular Device Japan K.K.).

Specifically, the recovery rate was calculated using the following formula (1), wherein the antibody-containing solution concentration was C0, the antibody-containing solution volume was V0, and the antibody monomer proportion obtained by size exclusion chromatography was R0, before passing through polyamide membrane 1, and similarly, the antibody-containing solution concentration was C1, the antibody-containing solution volume was V1, and the antibody monomer proportion obtained by size exclusion chromatography was R1, after passing through polyamide membrane 1.

The calculation results are shown in [Table 1] below.

Antibody monomer recovery rate (%)=C1V1R1/ C0V0R0      (Formula (1))

Comparative Example 1

Polyamide membrane 2 prepared under the same conditions as in polyamide membrane 1 except that the polyamide membrane was not immersed in a sodium hydroxide aqueous solution was used.

In Comparative Example 1, the polyamide membrane was immersed in water.

The operation was carried out with the other conditions being the same as in Example 1.

The analysis results by size exclusion chromatography after passing through polyamide membrane 2 and the antibody monomer recovery rate are shown in [Table 1] below.

TABLE 1

|  | Proportion (%) | | | Antibody monomer recovery rate (%) |
| --- | --- | --- | --- | --- |
|  | Monomer | Dimer | Trimer or higher multimer aggregate | |
| SM | 96.87 | 0.99 | 2.14 | — |
| Example 1 | 98.2 | 0.70 | 1.02 | 97.9 |
| Comparative Example 1 | 98.3 | 0.72 | 0.98 | 95.4 |

When comparing the results of Example 1 and Comparative Example 1, it was found that the antibody monomer recovery rate was improved while the amount of the antibody aggregate removed was maintained, by the treatment of immersing the polyamide membrane in the sodium hydroxide aqueous solution.

Example 2

(1) Alkaline Aqueous Solution Treatment of Polyamide Membrane as Polyamide Medium Polyamide membranes 3 to 6 and polyamide membrane 8 were prepared in the same manner as in "(1) Immersion of polyamide membrane as polyamide medium in alkaline aqueous solution" in [Example 1] above except that the immersion solution in a sodium hydroxide solution and the immersion time were changed.

Polyamide membrane 7 was prepared by setting two of the same polyamide membranes as in [Example 1] (Whatman (registered trademark): 7402-002, manufactured by GE Healthcare, material: polyamide 66) in a stainless holder KS-25 (manufactured by Advantech, effective membrane area of 3.8 cm²) in the same manner as in [Example 1] above, subsequently passing a 0.5 mol/L sodium hydroxide solution at a flow rate of 1.1 mL/min at room temperature for 1 hour using an AKTA purifier (manufactured by GE Healthcare), which is a separation/purification apparatus, and then passing pure water to completely remove sodium hydroxide.

The polyamide membranes prepared are shown in [Table 2] below.

TABLE 2

|  | Polyamide membrane 3 | Polyamide membrane 4 | Polyamide membrane 5 | Polyamide membrane 6 | Polyamide membrane 7 | Polyamide membrane 8 | Polyamide membrane α |
|---|---|---|---|---|---|---|---|
| Immersion solution | 1M NaOH | 0.1M NaOH | 1M NaOH | 0.5M NaOH | 0.5M NaOH | 1M NaOH | Water |
| Immersion time | 16 h | 16 h | 1 h | 1 h | 1 h (Liquid passage) | 40 h | 16 h |
| Temperature | 20° C. | 20° C. | 20° C. | 20° C. | 20° C. | 20° C. | 20° C. |

(2) Passage of Antibody-Containing Solution Through Polyamide Membrane

The solution obtained in ((2) Preparation of antibody-containing solution) and ((3) Purification of antibody-containing solution using affinity column) in [Example 1] above was buffer-exchanged to a 15 mmol/L tris-HCl buffer solution (pH 7.0, 5 mS/cm) to obtain an antibody-containing solution.

The antibody-containing solution was passed through polyamide membranes 3 to 7 obtained in ((1) Alkaline aqueous solution treatment of polyamide membrane as polyamide medium) in [Example 2] above using an AKTA purifier at a flow rate of 0.6 mL/min, and the antibody-containing solution was recovered.

When a 15 mmol/L tris-HCl buffer solution (pH 7.0, 5 mS/cm) was passed through polyamide membranes 3 to 7 obtained above before passing the antibody-containing solution, and the recovered solution was analyzed using a spectrophotometer; NanoDrop One (manufactured by Thermo Fisher Scientific Inc.), absorption of light having a wavelength of 280 nm, which is generally absorbed by a compound having a benzene ring such as a protein, was not confirmed.

Because of this, it was determined that there was no elution of a compound that absorbs light having a wavelength of 280 nm from the polyamide membrane before passing through the antibody-containing solution, and that the light absorption of the solution recovered by passing the antibody-containing solution through the polyamide membrane was derived from the antibody.

(3) Evaluation of Antibody Monomer Recovery Rate

The aggregate proportions and antibody concentrations of the antibody-containing solution prepared in (2) of [Example 2] above and the antibody-containing solution recovered by passing through the polyamide membrane in (2) of [Example 2] were measured.

From the obtained measured values, the mass of the antibody monomer in the antibody-containing solution prepared, the mass of the antibody monomer adsorbed on each polyamide membrane, and the recovery rate of the antibody monomer were calculated.

Specifically, the mass of the antibody monomer in the antibody-containing solution prepared and the mass of the antibody monomer adsorbed on each polyamide membrane were determined by the following formulas (2) and (3), respectively.

In (2) and (3) below, the antibody-containing solution concentration was C2, the antibody-containing solution volume was V2, and the antibody monomer proportion obtained by size exclusion chromatography was R2, before passing through polyamide membranes 3 to 8, and similarly, the antibody-containing solution concentration was C3, the antibody-containing solution volume was V3, and the antibody monomer proportion was R3, after passing through polyamide membranes 3 to 8.

The recovery rate of the antibody monomer was calculated in the same manner as in ((9) Calculation of antibody monomer recovery rate) in [Example 1] above.

The calculation results are shown in [Table 3] below.

$$\text{Mass (mg) of antibody monomer in antibody-containing solution prepared} = C2V2R2 \quad \text{(Formula (2))}$$

$$\text{Mass (mg) of antibody monomer adsorbed on polyamide membrane} = C2V2R2 - C3V3R3 \quad \text{(Formula (3))}$$

As methods for measuring the aggregate proportion in the antibody-containing solution and the antibody concentration, the former was measured by the same method as in ((8) Specific evaluation of aggregate removal performance) of [Example 1] above, and the latter was measured using a spectrophotometer; NanoDrop One (manufactured by Thermo Fisher Scientific Inc.).

Comparative Example 2

Polyamide membrane α was prepared in the same manner as in polyamide membrane 3 except that the polyamide membrane was not immersed in a sodium hydroxide aqueous solution.

In Comparative Example 2, the polyamide membrane was immersed in water.

The conditions for preparing polyamide membrane α are shown in [Table 2] above.

The same operation as in [Example 2] above was carried out on polyamide membrane α.

The antibody monomer recovery rate is shown in [Table 3] below.

TABLE 3

|  |  | Antibody monomer mass (mg) | Antibody monomer recovery rate (%) |
|---|---|---|---|
|  | Antibody-containing solution prepared | 10.04 | — |
| Example 2 | Polyamide membrane 3 adsorbed | 0.40 | 96.0 |
|  | Polyamide membrane 4 adsorbed | 0.40 | 96.0 |
|  | Polyamide membrane 5 adsorbed | <0.05 | 99.5< |
|  | Polyamide membrane 6 adsorbed | <0.05 | 99.5< |
|  | Polyamide membrane 7 adsorbed | <0.05 | 99.5< |
|  | Polyamide membrane 8 adsorbed | 0.14 | 98.6 |
| Comparative Example 2 | Polyamide membrane α adsorbed | 1.11 | 89.0 |

When comparing the results of Example 2 and Comparative Example 2, it was found that the antibody monomer recovery rate was improved by immersing the polyamide membrane in the sodium hydroxide aqueous solution.

Polyamide membranes 3 to 6 and polyamide membrane 8 each had a higher antibody monomer recovery rate than polyamide membrane α, and thus it became clear that the effect of improving the antibody monomer recovery rate of the polyamide medium of the present invention depended on neither of the pH of the alkaline solution and the immersion time.

In addition, the same effect was also obtained in polyamide membrane 7, and thus it was shown that the effect of improving the antibody monomer recovery rate of the polyamide medium of the present invention did not depend on the method for alkaline solution treatment.

Example 3

Polyamide membranes 3 to 5 and polyamide membrane 8 were subjected to the same experiment as in [Example 2] except that the pH of the antibody-containing solution, the electrical conductivity, and the buffer solution were changed.

For an antibody-containing solution, the antibody-containing solution obtained in ((2) Preparation of antibody-containing solution) and ((3) Purification of antibody-containing solution using affinity column) in [Example 1] above was buffer-exchanged to a 15 mmol/L acetate buffer solution (pH 5.5, 15 mS/cm) to obtain an antibody-containing solution.

The calculation results of the antibody monomer recovery rates are shown in [Table 4] below.

Comparative Example 3

The same operation as in [Example 3] above was carried out on polyamide membrane α prepared in [Comparative Example 2] above.

The calculation result of the antibody monomer recovery rate is shown in [Table 4] below.

TABLE 4

| | | Antibody monomer mass (mg) | Antibody monomer recovery rate (%) |
|---|---|---|---|
| | Antibody-containing solution prepared | 10.3 | — |
| Example 3 | Polyamide membrane 3 adsorbed | <0.05 | 99.5< |
| | Polyamide membrane 4 adsorbed | 0.08 | 99.2 |
| | Polyamide membrane 5 adsorbed | <0.05 | 99.5< |
| | Polyamide membrane 8 adsorbed | <0.05 | 99.5< |
| Comparative Example 3 | Polyamide membrane α adsorbed | 0.13 | 98.7 |

When comparing the results of Example 3 and Comparative Example 3, it was found that the antibody monomer recovery rate was improved by immersing the polyamide membrane in the sodium hydroxide aqueous solution.

By comparing the results of Examples 2 and 3 with those of Comparative Examples 2 and 3, it was found that the effect of increase in the amount of the antibody monomer recovered by immersing the polyamide membrane in the aqueous sodium hydroxide solution can be obtained regardless of the condition of the antibody-containing solution.

Example 4

The same experiment as in [Example 3] above except that the antibody type of the antibody-containing solution was changed was carried out.

Evolocumab (manufactured by Astellas Pharma Inc.) was buffer-exchanged to a 15 mmol/L acetate buffer solution (pH 5.5, 15 mS/cm) to obtain an antibody-containing solution.

The calculation results of the antibody monomer recovery rates are shown in [Table 5] below.

Comparative Example 4

The same operation as in [Example 4] above was carried out on polyamide membrane a prepared in [Comparative Example 2] above.

The calculation result of the antibody monomer recovery rate is shown in [Table 5] below.

TABLE 5

| | | Antibody monomer mass (mg) | Antibody monomer recovery rate (%) |
|---|---|---|---|
| | Antibody-containing solution prepared | 10.29 | — |
| Example 4 | Polyamide membrane 3 adsorbed | 0.29 | 97.2 |
| | Polyamide membrane 4 adsorbed | 0.38 | 96.4 |
| | Polyamide membrane 5 adsorbed | 0.44 | 95.7 |
| | Polyamide membrane 8 adsorbed | 0.90 | 91.2 |
| Comparative Example 4 | Polyamide membrane α adsorbed | 1.77 | 82.8 |

When comparing the results of Example 4 and Comparative Example 4, it was found that the antibody monomer recovery rate was improved by immersing the polyamide membrane in the sodium hydroxide aqueous solution.

By comparing the results of Examples 3 and 4 with those of Comparative Examples 3 and 4, it was found that the effect of increase in the amount of the antibody monomer recovered by immersing the polyamide membrane in the aqueous sodium hydroxide solution can be obtained regardless of the antibody type.

Example 5

The same experiment as in [Example 4] above except that the method for preparing the polyamide membrane was changed was carried out.

Specifically, polyamide membranes 9 to 11 were prepared in the same manner as in (Alkaline aqueous solution treatment of polyamide membrane as polyamide medium in [Example 1]) above except that the immersion solution and the immersion time were changed.

The conditions for preparing the polyamide membranes are shown in [Table 6] below.

In addition, the calculation results of the antibody monomer recovery rates are shown in [Table 7] below.

TABLE 6

| | Polyamide membrane 9 | Polyamide membrane 10 | Polyamide membrane 11 | Polyamide membrane α |
|---|---|---|---|---|
| Immersion solution | 0.01M NaOH | 0.5M NaOH | 1M HCl | Water |
| Immersion time | 16 h | 0.5 h | 16 h | 16 h |
| Temperature | 20° C. | 20° C. | 20° C. | 20° C. |

Comparative Example 5

Polyamide membrane α prepared under the same conditions as in polyamide membranes 9 to 11 in [Example 5] above except that the polyamide membrane was not immersed in a sodium hydroxide aqueous solution was used.

In Comparative Example 5, the polyamide membrane was immersed in water.

The same operation as in [Example 5] above was carried out on polyamide membrane α. The conditions for preparing the polyamide membrane are shown in [Table 6] above.

In addition, the antibody monomer recovery rate is shown in [Table 7] below.

TABLE 7

|  |  | Antibody monomer mass (mg) | Antibody monomer recovery rate (%) |
|---|---|---|---|
|  | Antibody-containing solution prepared | 10.13 | — |
| Example 5 | Polyamide membrane 9 adsorbed | 0.85 | 91.6 |
|  | Polyamide membrane 10 adsorbed | 0.54 | 94.7 |
|  | Polyamide membrane 11 adsorbed | 0.85 | 91.6 |
| Comparative Example 5 | Polyamide membrane α adsorbed | 0.95 | 90.7 |

When comparing the results of Example 5 and Comparative Example 5, it was found that the antibody monomer recovery rate was improved by immersing the polyamide membrane in the sodium hydroxide aqueous solution.

From this, it was found that in the present invention, the effect of improving the antibody monomer recovery rate can be obtained regardless of whether the solution used for treating the polyamide medium is an acidic aqueous solution or an alkaline aqueous solution and that the immersion solution concentration and the immersion time are not limited.

Example 6

The same experiment as in [Example 4] above except that only the method for preparing the polyamide membrane was changed was carried out.

Polyamide membrane 12 was prepared in the same manner as in ((1) Immersion of polyamide membrane as polyamide medium in alkaline aqueous solution) in [Example 1] above except that only the immersion temperature was changed.

The conditions for preparing the polyamide membrane are shown in [Table 8] below.

In addition, the calculation result of the antibody monomer recovery rate is shown in [Table 9] below.

TABLE 8

|  | Polyamide membrane 12 | Polyamide membrane β |
|---|---|---|
| Immersion solution | 1M NaOH | Water |
| Immersion time | 16 h | 16 h |
| Temperature | 4° C. | 4° C. |

Comparative Example 6

Polyamide membrane β prepared under the same conditions as in polyamide membrane 12 except that the polyamide membrane was not immersed in a sodium hydroxide aqueous solution was used.

In Comparative Example 6, the polyamide membrane was immersed in water.

The same operation as in [Example 6] above was carried out on polyamide membrane β.

The conditions for preparing the polyamide membrane are shown in [Table 8] above.

In addition, the antibody monomer recovery rate is shown in [Table 9] below.

TABLE 9

|  |  | Antibody monomer mass (mg) | Antibody monomer recovery rate (%) |
|---|---|---|---|
|  | Antibody-containing solution prepared | 10.13 | — |
| Example 6 | Polyamide membrane 12 adsorbed | 0.54 | 94.6 |
| Comparative Example 6 | Polyamide membrane β adsorbed | 0.73 | 92.8 |

When comparing the results of Example 6 and Comparative Example 6, it was found that the antibody monomer recovery rate was improved by immersing the polyamide membrane in the sodium hydroxide aqueous solution.

From this, it was found that in the present invention, the desired effect can be obtained without being limited by the treatment temperature with the aqueous sodium hydroxide solution.

Example 7

(1) Immersion of Polyamide Membrane in Alkaline Aqueous Solution

A polyamide membrane as a porous polyamide medium having a circular shape having a diameter of 9.0 cm, a membrane thickness of 170 μm, and an average pore diameter of 0.2 μm (Whatman (registered trademark): 7402-009, manufactured by GE Healthcare, material: polyamide 66) was immersed in a 1.0 mol/L sodium hydroxide solution (pH 14) at room temperature for 1 hour.

Next, the polyamide membrane was washed with pure water 5 times to completely remove sodium hydroxide.

The polyamide membrane obtained was purged with methanol, and the solvent was completely removed by vacuum drying to obtain polyamide membrane 13.

In addition, polyamide membranes 14 and 15 were prepared under the same conditions as described above except that the immersion time was changed.

The conditions for preparing the polyamide membranes are shown in [Table 10] below.

(2) Evaluation of Tensile Strength of Polyamide Membrane

Sections of the polyamide membranes obtained above were prepared in such a way as to form a rectangle of 2.0 cm×7.0 cm.

The tensile strength of the prepared sections was evaluated using a tensile compression tester; TG-1KN (manufactured by Minebea Co., Ltd.).

In this evaluation, the environment of the room in which the measurement was carried out was such that the temperature was 22.5° C. and the humidity was 35 to 40%, and the measurement conditions were such that the tensile speed was 10 mm/min and the initial length was 6.0 cm.

The measurement results are shown in [Table 11] below. The numerical values of each parameter indicate the average value and the standard error when the test thereof was carried out 6 times.

The Young's modulus indicates the slope in the elastic region when the stress applied to a sample and the strain are plotted, and the maximum stress indicates the maximum value of the stress applied to the sample from the start of the test to the fracture of the sample.

TABLE 10

|  | Polyamide membrane 13 | Polyamide membrane 14 | Polyamide membrane 15 | Polyamide membrane γ |
|---|---|---|---|---|
| Immersion solution | 1M NaOH | 1M NaOH | 1M NaOH | Water |
| Immersion time | 1 h | 16 h | 40 h | 16 h |
| Temperature | 20° C. | 20° C. | 20° C. | 20° C. |

Comparative Example 7

Polyamide membrane γ prepared under the same conditions as in polyamide membrane 13 except that the polyamide membrane was not immersed in a sodium hydroxide aqueous solution was used.

In Comparative Example 7, the polyamide membrane was immersed in water.

The operation was carried out with the other conditions being the same as in Example 7 above.

The conditions for preparing polyamide membrane γ are shown in [Table 10] above.

The measurement results are shown in [Table 11] below.

TABLE 11

|  |  | Young's modulus (N) | Maximum stress (N) |
|---|---|---|---|
| Example 7 | Polyamide membrane 13 | 558.2 ± 53.1 | 17.3 ± 0.7 |
|  | Polyamide membrane 14 | 594.8 ± 36.7 | 18.7 ± 0.8 |
|  | Polyamide membrane 15 | 536.7 ± 36.7 | 18.3 ± 0.5 |
| Comparative Example 7 | Polyamide membrane γ | 596.4 ± 38.2 | 18.5 ± 1.0 |

When comparing the results of Example 7 and Comparative Example 7, it was found that the Young's modulus and the maximum stress of the polyamide membrane do not change regardless of the presence or absence of immersion in the sodium hydroxide aqueous solution.

That is, according to the present invention, it was found that a practically sufficient mechanical strength can be maintained.

In the production step of a protein preparation such as an antibody drug, particularly a virus removal filter and a prefilter thereof are required to have the following properties: a membrane is not easily deformed even when a pressure is applied to the membrane and is not easily torn even when a high pressure is applied to the membrane. From this viewpoint, it was found that both the Young's modulus and the maximum stress do not change even in the case of immersion in an alkaline aqueous solution and that the membrane strength can be maintained as a protein purification filter, which is practically preferable.

Example 8

(1) Immersion of Polyamide Membrane in Alkaline Aqueous Solution

A polyamide membrane as a porous polyamide medium having a circular shape having a diameter of 2.5 cm, a film thickness of 160 μm, and an average pore diameter of 0.2 μm (Whatman (registered trademark): 7402-002, manufactured by GE Healthcare) was immersed in a 1.0 mol/L sodium hydroxide solution (pH 14) at room temperature for 1 hour.

Next, the polyamide membrane was washed with pure water 5 times to completely remove sodium hydroxide.

The polyamide membrane obtained was purged with methanol, and the solvent was completely removed by vacuum drying to obtain polyamide membrane 16. The conditions for preparing the polyamide membrane are shown in [Table 12] below.

TABLE 12

|  | Polyamide membrane 16 | Polyamide membrane δ |
|---|---|---|
| Immersion solution | 1M NaOH | Water |
| Immersion time | 1 h | 1 h |
| Temperature | 20° C. | 20° C. |

(2) Measurement of Weight Average Molecular Weight and Number Average Molecular Weight of Polyamide Membrane Using any of the polyamide membranes obtained in (1) above as a sample, the molecular weight thereof was measured by gel permeation chromatography (GPC).

About 5 mg of the polyamide membrane was measured out, 5 mL of 5 mmol/L Na trifluoroacetate (HFIP) was added thereto, and then the resulting mixture was allowed to stand overnight.

After confirming that the sample was completely dissolved, the sample was filtered using a 0.45 μm (polytetrafluoroethylene, PTFE) filter, and the filtrate was used as a measurement sample.

The measurement results are shown in [Table 13] below (Mw: weight average molecular weight, Mn: number average molecular weight).

<Measurement Conditions>
Measuring apparatus: HLC-8320GPC (manufactured by Tosoh Corporation)
Column: 3×TSKgel GMH$_{HR}$-H(S) (4.6 mm I.D.×15 cm)
Column temperature: 40° C.
Eluent: 5 mmol/L Na trifluoroacetate
Calibration curve: polymethyl methacrylate (12 points)

Comparative Example 8

Polyamide membrane δ prepared under the same conditions as in polyamide membrane 16 except that the polyamide membrane was not immersed in a sodium hydroxide aqueous solution was used.

In Comparative Example 8, the polyamide membrane was immersed in water.

The operation was carried out with the other conditions being the same as in Example 8 above.

The conditions for preparing the polyamide membrane are shown in [Table 12] above.

The measurement results are shown in [Table 13] below.

TABLE 13

|  | n | Mw | Mn |
|---|---|---|---|
| Example 8 | 1 | 108140 | 33178 |
|  | 2 | 112574 | 32021 |
| Comparative Example 8 | 1 | 112123 | 31737 |
|  | 2 | 113847 | 30603 |

When comparing the results of Example 8 and Comparative Example 8, it was found that the weight average molecular weight and the number average molecular weight are not affected even if the polyamide membrane is immersed in the sodium hydroxide aqueous solution. This means that hydrolysis by alkaline immersion has not progressed to the inside of the polyamide membrane. Moreover, the results of Examples 1 to 6 and Comparative Examples 1 to 6 show that the behavior of adsorption of the antibody on the polyamide membrane changes depending on the presence or absence of the treatment with the alkaline aqueous solution, and thus properties of the surface of the polyamide membrane have changed.

Therefore, from the results of Examples 1 to 6, Example 8, and Comparative Examples 1 to 6, and Comparative Example 8, it was found that the treatment with the alkaline aqueous solution changes properties of the surface of the polyamide membrane, but does not affect properties of the inside thereof.

Example 9

(1) Immersion of Polyamide Membrane in Alkaline Aqueous Solution

Polyamide membrane 17 was prepared in the same manner as in ((1) immersion of polyamide membrane in alkaline aqueous solution) in [Example 8] above except that the immersion time of the aqueous sodium hydroxide solution was 40 hours.

The conditions for preparing polyamide membrane 17 are shown in [Table 14] below.

TABLE 14

|  | Polyamide membrane 17 | Polyamide membrane ε |
|---|---|---|
| Immersion solution | 1M NaOH | Water |
| Immersion time | 40 h | 40 h |
| Temperature | 20° C. | 20° C. |

(2) XPS Measurement of Polyamide Membrane

A small piece that was about 2 mm square was cut out from the polyamide membrane obtained in (1) above and immersed in 60 mL of a $0.5 \times 10^{-4}$ mol/dm$^3$ $Rb_2CO_3$ aqueous solution for 2 hours.

The piece was transferred to a 1.5 mL sample tube (having an underlay of absorbent cotton), centrifuged at 10000 rpm for 10 minutes, and subjected to XPS measurement. The measurement results are shown in [Table 15] below.

Equipment used: PHI5000 Versa Probe II (manufactured by ULVAC-PHI, Inc.)

Excitation source: mono. AlKα 20 kV×5 mA 100 W

Analysis size: 100 μm×1.4 mm (when capturing data, vibrates 100 μmφ mono. AlKα at a width of 1.4 mm)

Photoelectron extraction angle: 45°

Capture area: Rb 3d

Pass Energy: 93.9 eV

Comparative Example 9

Polyamide membrane ε prepared under the same conditions as in polyamide membrane 17 except that the polyamide membrane was not immersed in a sodium hydroxide aqueous solution was used.

In Comparative Example 9, the polyamide membrane was immersed in water.

The operation was carried out with the other conditions being the same as in Example 9 above.

The conditions for preparing polyamide membrane ε are shown in [Table 14] above.

The measurement results are shown in [Table 15] below.

TABLE 15

|  | Measurement surface |  | Relative element concentration (atomic %) Rb |
|---|---|---|---|
| Example 9 | Surface | 1st place | 0.01 |
|  |  | 2nd place | 0.01 |
|  |  | 3rd place | 0.02 |
|  |  | 4th place | 0.03 |
| Comparative Example 9 | Surface | 1st place | n.d. |
|  |  | 2nd place | n.d. |
|  |  | 3rd place | n.d. |
|  |  | 4th place | n.d. |

When comparing the results of Example 9 and Comparative Example 9, it was found that the rubidium concentration on the surface of the polyamide membrane was increased by treating the polyamide membrane with an alkaline aqueous solution. From this, it was found that the amount of carboxyl groups on the surface was increased by treating the polyamide membrane with the alkaline aqueous solution. That is, it was found that the treatment with the alkaline aqueous solution hydrophilized the surface of the polyamide membrane, leading to an increase in the amount of the target protein recovered.

Example 10

(1) Immersion of Polyamide Sheet in Alkaline Aqueous Solution

A 66 nylon sheet (model number: 107-14301, thickness: 0.3 mm, manufactured by KOKUGO Co., Ltd.) was immersed in a 1.0 mol/L sodium hydroxide aqueous solution (pH 14) at room temperature for 13 days.

Next, the sheet was washed with pure water 5 times to completely remove sodium hydroxide.

The resulting sheet was immersed in a 0.001 mol/L hydrochloric acid solution for 1 hour, washed with distilled water, and air-dried to obtain polyamide sheet (1).

The conditions for preparing polyamide sheet (1) are shown in [Table 16] below.

TABLE 16

|  | Polyamide sheet (1) | Polyamide sheet (2) |
|---|---|---|
| Immersion solution | 1M NaOH | Water |
| Immersion time | 13 days | 13 days |
| Temperature | 20° C. | 20° C. |

(2) FT-IR Measurement of Polyamide Sheet

Polyamide sheet (1) obtained in (1) above was used as a measurement sample, and the sample was measured by Fourier transform infrared spectroscopy (FT-IR) under the following conditions.

Figure 3:
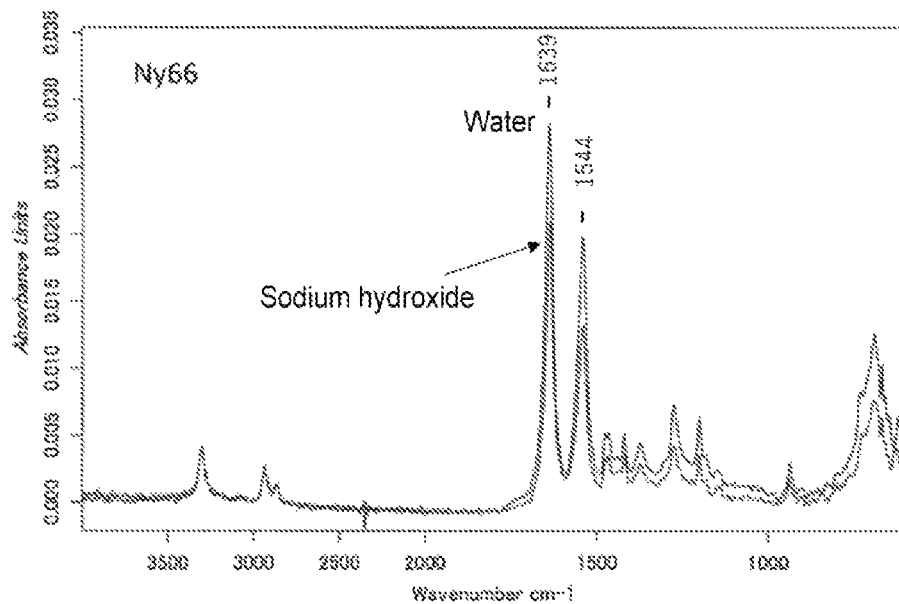
FIG. 3 shows spectra of FT-IR of Example 10 and Comparative Example 10. The one having the larger peaks at 1639 cm$^{-1}$ and 1544 cm$^{-1}$ (the one with "Water") shows the measurement result of Comparative Example 10, and the one having the smaller peaks (the one with "Sodium hydroxide") shows the measurement result of Example 10.

The measurement results are shown in FIG. 3.

<Measurement Conditions>
  Measuring apparatus: ALPHA (Bruker Corporation)
  Measurement method: ATR method (crystal: Ge)
  Resolution: 4 cm$^{-1}$
  Number of scans: 16 scans Comparative Example 10

Polyamide sheet (2) was prepared under the same conditions as polyamide sheet (1) in [Example 10] above except that the polyamide sheet was not immersed in an aqueous sodium hydroxide solution, and was used as a measurement sample.

In Comparative Example 10, the polyamide sheet was immersed in water.

The operation was carried out with the other conditions being the same as in Example 10 above.

The conditions for preparing polyamide sheet (2) are shown in [Table 16] above.

The measurement results are shown in FIG. 3.

In FIG. 3, "sodium hydroxide" refers to the measurement result of polyamide sheet (1) that was immersed in the sodium hydroxide aqueous solution, and in FIG. 3, "water" refers to the measurement result of polyamide sheet (2) that was not immersed in a sodium hydroxide aqueous solution and was immersed in water.

When comparing the results of Example 10 and Comparative Example 10, it was found that the peak intensities at 1639 cm$^{-1}$ and 1544 cm$^{-1}$ were reduced by treating the polyamide sheet with the alkaline aqueous solution. From this, it was found that the amide bond on the surface was reduced by the treatment of the polyamide sheet with the alkaline aqueous solution.

When these results were combined with the results of Example 8 and Comparative Example 8, it was found that hydrolysis progressed on the surface of the polyamide sheet because of the treatment with the alkaline aqueous solution.

The present application is based on a Japanese patent application filed with the Japan Patent Office on Apr. 8, 2019 (Japanese Patent Application No. 2019-073514), and a Japanese patent application filed with the Japan Patent Office on Nov. 6, 2019 (Japanese Patent Application No. 2019-201725), the contents of which are incorporated herein by reference.

INDUSTRIAL APPLICABILITY

The method for producing a polyamide medium for purifying a protein-containing solution according to the present invention has industrial applicability in the field of an antibody-containing solution production technology in which the selectivity for removing an antibody aggregate is improved.

The invention claimed is:

1. A method for purifying a protein-containing solution, comprising:
    treating a polyamide medium before an alkali treatment, with an alkaline aqueous solution having a pH of 10 or more under conditions of 4° C. or more and 100° C. or less and 5 minutes or more and 70 hours or less;
    cleaning the polyamide medium;
    contacting a protein-containing solution with the polyamide medium after the cleaning; and
    recovering the purified protein-containing solution.

2. The method for purifying a protein-containing solution according to claim 1,
    wherein the protein-containing solution is an antibody-containing solution.

3. The method for purifying a protein-containing solution according to claim 2,
    wherein the antibody-containing solution includes an antibody aggregate, the method comprising:
    removing the antibody aggregate from the antibody-containing solution.

4. The method according to claim 1, wherein
    wherein a protein recovery rate of the polyamide medium after the treatment is higher than a protein recovery rate of the polyamide medium before the treatment.

5. The method according to claim 1,
    wherein the pH of the alkaline aqueous solution is greater than 13.

6. The method according to claim 1,
    wherein the pH of the alkaline aqueous solution is 13.5 or greater.

* * * * *

UNITED STATES PATENT AND TRADEMARK OFFICE
CERTIFICATE OF CORRECTION

| | | |
|---|---|---|
| PATENT NO. | : 12,383,884 B2 | Page 1 of 1 |
| APPLICATION NO. | : 17/601834 | |
| DATED | : August 12, 2025 | |
| INVENTOR(S) | : H. Taniguchi et al. | |

It is certified that error appears in the above-identified patent and that said Letters Patent is hereby corrected as shown below:

On the Title Page

Page 2/item (56) Foreign Pat. Docs. (Column 2, Line 16), please change "2018-00772" to -- 2018-040772 --.

Signed and Sealed this
Eleventh Day of November, 2025

John A. Squires
*Director of the United States Patent and Trademark Office*